US007259001B2

(12) United States Patent
Cheung

(10) Patent No.: US 7,259,001 B2
(45) Date of Patent: *Aug. 21, 2007

(54) METHODS AND COMPOSITIONS FOR TREATING MALE SEXUAL DYSFUNCTION

(75) Inventor: Ling Yuk Cheung, Hong Kong (HK)

(73) Assignee: Ultra Biotech Limited, Douglas (IM)

( * ) Notice: Subject to any disclaimer, the term of this patent is extended or adjusted under 35 U.S.C. 154(b) by 314 days.

This patent is subject to a terminal disclaimer.

(21) Appl. No.: 10/717,158

(22) Filed: Nov. 18, 2003

(65) Prior Publication Data

US 2005/0106173 A1    May 19, 2005

(51) Int. Cl.
*C12N 1/14* (2006.01)
*C12N 13/00* (2006.01)

(52) U.S. Cl. ................ 435/173.1; 435/255.1; 435/255.2; 435/173.8

(58) Field of Classification Search ........... 424/195.16; 435/254.2, 254.21, 173.1, 173.8, 255.1, 255.2
See application file for complete search history.

(56) References Cited

U.S. PATENT DOCUMENTS

| | | | |
|---|---|---|---|
| 2,107,830 A | 2/1938 | Liebesny et al. | |
| 3,150,979 A | 9/1964 | Ensley | |
| 3,711,392 A | 1/1973 | Metzger | |
| 3,870,599 A | 3/1975 | Azarowicz | |
| 3,923,279 A | 12/1975 | Gresley et al. | |
| 3,939,279 A | 2/1976 | Kawano et al. | |
| 3,968,254 A | 7/1976 | Rhodes et al. | |
| 3,997,675 A | 12/1976 | Eichelburg | |
| 4,041,182 A | 8/1977 | Erickson et al. | |
| 4,081,367 A | 3/1978 | Hulls et al. | 210/610 |
| 4,118,512 A | 10/1978 | Eichelburg | |
| 4,183,807 A | 1/1980 | Yoshizawa et al. | 210/611 |
| 4,211,645 A | 7/1980 | Zajic et al. | 210/611 |
| 4,348,483 A | 9/1982 | Skogerson | |
| 4,559,305 A | 12/1985 | Zajic et al. | 435/243 |
| 4,816,158 A | 3/1989 | Shimura et al. | 210/610 |
| 5,047,250 A | 9/1991 | Prieels et al. | |
| 5,075,008 A | 12/1991 | Chigusa et al. | 210/610 |
| 5,082,662 A | 1/1992 | Laurent et al. | |
| 5,082,936 A | 1/1992 | Jamas et al. | |
| 5,106,594 A | 4/1992 | Held et al. | 422/292 |
| 5,158,788 A | 10/1992 | Lavens et al. | |
| 5,416,010 A | 5/1995 | Langenberg et al. | 435/468 |
| 5,476,787 A | 12/1995 | Yokoyama et al. | 435/262.5 |
| 5,504,079 A | 4/1996 | Jamas et al. | |
| 5,567,314 A | 10/1996 | Chigusa et al. | 210/150 |
| 5,578,486 A | 11/1996 | Zhang | 435/243 |
| 5,665,352 A | 9/1997 | Blehaut et al. | |
| 5,707,524 A | 1/1998 | Potter | 210/606 |
| 5,866,116 A | 2/1999 | Yaegaki | |
| 5,879,928 A | 3/1999 | Dale et al. | 435/264 |
| 5,952,020 A | 9/1999 | Lizak | |
| 5,981,219 A | 11/1999 | Flugge et al. | |
| 6,036,854 A | 3/2000 | Potter | 210/177 |
| 6,045,834 A | 4/2000 | Howes et al. | |
| 6,143,731 A | 11/2000 | Jamas et al. | |
| 6,159,510 A | 12/2000 | Lizak | |
| 6,197,295 B1 | 3/2001 | Hsia et al. | |
| 6,214,337 B1 | 4/2001 | Hayen et al. | |
| 6,391,617 B1 | 5/2002 | Cheung | 435/254 |
| 6,391,618 B1 | 5/2002 | Cheung | 435/255 |
| 6,391,619 B1 | 5/2002 | Cheung | 435/255 |
| 6,416,982 B1 | 7/2002 | Zhang | |
| 6,416,983 B1 | 7/2002 | Cheung | |
| 6,436,695 B1 | 8/2002 | Cheung | 435/254 |
| 6,440,713 B1 | 8/2002 | Cheung | 435/173 |
| 6,596,272 B2 | 7/2003 | Cheung | |
| 6,596,273 B2 | 7/2003 | Cheung | |
| 6,649,383 B1 | 11/2003 | Cheung | 435/173.1 |
| 6,660,508 B1 | 12/2003 | Cheung | 435/173.1 |
| 6,699,496 B1 | 3/2004 | Kojima et al. | |
| 6,761,886 B2 | 7/2004 | Cheung | |
| 6,800,466 B2 | 10/2004 | Cheung | |
| 6,828,131 B2 | 12/2004 | Zhang | |
| 6,828,132 B2 | 12/2004 | Cheung | |

(Continued)

FOREIGN PATENT DOCUMENTS

CN        1110317 A      10/1995

(Continued)

OTHER PUBLICATIONS

Dutta et al. J. Microwave Power (1979), vol. 14, No. 3, pp. 275-280.*
"*Saccharomyces cerevisiae* Meyen ex Hansen Chinese Strain name"http:www.im/ac/cn/database/CCCCM/Yeast?y133.htm). Apr. 24, 1996.*
Agarwal N. et al., "Selection of *Saccharomyces cerevisiae* strains for use as a microbial feed additive," *Letters in Applied Microbiology*, 31:270-273 (2000).
Asami, K. et al., "Real-Time Monitoring of Yeast Cell Division by Dielectric Spectroscopy", *Biophysical Journal*, 76, pp. 3345-3348 (1999).
Balcer-Kubiczek, E.K. et al., "Expression Analysis of Human HL60 Cells Exposed to 60 Hz Square-or Sine-Wave Magnetic Fields", *Radiation Research*, 153, pp. 670-678 (2000).

(Continued)

*Primary Examiner*—Christopher R Tate
*Assistant Examiner*—Randall Winston
(74) *Attorney, Agent, or Firm*—Fish & Neave IP Group of Ropes & Gray LLP

(57) ABSTRACT

The invention provides compositions comprising a plurality of yeast cells, wherein said plurality of yeast cells are characterized by their ability to increase secretion of male hormones or alleviate or prevent sexual disorders, e.g., impotence, in a mammal, said ability resulting from their having been cultured in the presence of an alternating electric field having a specific frequency and a specific field strength. Also provided are methods of making and using these compositions.

5 Claims, 2 Drawing Sheets

U.S. PATENT DOCUMENTS

| | | | | |
|---|---|---|---|---|
| 7,041,677 | B2 * | 5/2006 | Cutler | 514/312 |
| 2002/0099026 | A1 | 7/2002 | Goodman et al. | |
| 2002/0123127 | A1 | 9/2002 | Cheung | 435/254 |
| 2002/0123129 | A1 | 9/2002 | Cheung | 435/254 |
| 2002/0123130 | A1 | 9/2002 | Cheung | 435/262 |
| 2003/0230126 | A1 | 12/2003 | Cheung | |
| 2003/0230245 | A1 | 12/2003 | Cheung | |
| 2003/0232038 | A1 | 12/2003 | Cheung | |
| 2003/0232039 | A1 | 12/2003 | Cheung | |
| 2003/0232059 | A1 | 12/2003 | Cheung | |
| 2003/0235565 | A1 | 12/2003 | Cheung | |
| 2003/0235566 | A1 | 12/2003 | Cheung | |
| 2003/0235567 | A1 | 12/2003 | Cheung | |
| 2003/0235568 | A1 | 12/2003 | Cheung | |
| 2003/0235569 | A1 | 12/2003 | Cheung | |
| 2003/0235570 | A1 | 12/2003 | Cheung | |
| 2004/0001812 | A1 | 1/2004 | Cheung | |
| 2004/0001813 | A1 | 1/2004 | Cheung | |
| 2004/0001814 | A1 | 1/2004 | Cheung | |
| 2004/0001815 | A1 | 1/2004 | Cheung | 424/93.51 |
| 2004/0001857 | A1 | 1/2004 | Cheung | 424/195.16 |
| 2004/0001858 | A1 | 1/2004 | Cheung | 424/195.16 |
| 2004/0001859 | A1 | 1/2004 | Cheung | 424/195.16 |
| 2004/0001860 | A1 | 1/2004 | Cheung | 424/195.16 |
| 2004/0001861 | A1 | 1/2004 | Cheung | 424/195.16 |
| 2004/0005335 | A1 | 1/2004 | Cheung | |
| 2004/0005337 | A1 | 1/2004 | Cheung | 424/195.16 |
| 2004/0005680 | A1 | 1/2004 | Cheung | |
| 2004/0168492 | A1 | 9/2004 | Cheung | |
| 2004/0253251 | A1 | 12/2004 | Cheung | |
| 2004/0253252 | A1 | 12/2004 | Cheung | |
| 2004/0253253 | A1 | 12/2004 | Cheung | |
| 2004/0253254 | A1 | 12/2004 | Cheung | |
| 2004/0253255 | A1 | 12/2004 | Cheung | |
| 2004/0253256 | A1 | 12/2004 | Cheung | |
| 2004/0253257 | A1 | 12/2004 | Cheung | |
| 2004/0253258 | A1 | 12/2004 | Cheung | |
| 2004/0253259 | A1 | 12/2004 | Cheung | |
| 2004/0253260 | A1 | 12/2004 | Cheung | |
| 2004/0253261 | A1 | 12/2004 | Cheung | |
| 2004/0253262 | A1 | 12/2004 | Cheung | |
| 2004/0253263 | A1 | 12/2004 | Cheung | |
| 2004/0253264 | A1 | 12/2004 | Cheung | |
| 2004/0253265 | A1 | 12/2004 | Cheung | |
| 2004/0253266 | A1 | 12/2004 | Cheung | |
| 2004/0253267 | A1 | 12/2004 | Cheung | |
| 2004/0253268 | A1 | 12/2004 | Cheung | |
| 2004/0265990 | A1 | 12/2004 | Cheung | |

FOREIGN PATENT DOCUMENTS

| | | | |
|---|---|---|---|
| CN | 1207873 | | 2/1999 |
| CN | 1309175 | * | 8/2001 |
| EP | 0041373 | | 12/1981 |
| EP | 553377 | | 8/1993 |
| EP | 1375652 | | 1/2004 |
| ES | 475500 | | 4/1979 |
| FR | 2222433 | | 10/1974 |
| GB | 1397873 | * | 6/1975 |
| JP | 60028893 | | 2/1985 |
| RU | 415983 A | | 11/1974 |
| RU | 1071637 | | 2/1984 |
| SU | 1722364 | | 3/1992 |
| SU | 1750570 | | 7/1992 |
| WO | WO87/02705 | | 2/1995 |
| WO | WO95/04814 | | 2/1995 |
| WO | WO99/60142 | | 11/1999 |
| WO | WO 02/20431 | | 3/2002 |
| WO | WO 02/062981 | | 8/2002 |
| WO | WO 02/062982 | | 8/2002 |
| WO | WO 02/062983 | | 8/2002 |
| WO | WO 02/062984 | | 8/2002 |
| WO | WO 02/062985 | | 8/2002 |
| WO | WO 02/070682 A2 | | 9/2002 |
| WO | WO02070436 | | 9/2002 |
| WO | WO02070683 | | 9/2002 |
| WO | WO2004108919 | | 12/2004 |

OTHER PUBLICATIONS

Bassett, C.A.L. et al., "Beneficial Effects of Electromagnetic Fields", *Journal of Cellular Biochemistry*, 51, pp. 387-393 (1993).

Binninger, D. M. et al., "Effects of 60Hz AC magnetic fields on gene expression following exposure over multiple cell generations using *Saccharomyces cerevisiae*", *Bioelectrochemistry and Bioenergetics*, 43(1): 83-89 (1997).

Conti, P. et al., "Effect of Electromagnetic Fields on Several CD Markers and Transcription and Expression of CD4", *Immunobiology*, 201, pp. 36-48 (1999).

Deguchi, T. et al., "Nylon biodegradation by lignin-degrading fungi", *Applied and Environmental Microbiology*, 63(1): 329-331 (1997).

Dufresne C. et al., "Tea, Kombucha, and Health: A review," *Food Research International*, 33:409-421 (2000).

Gonzalez, A.M. et al., "Effects of an Electric Field of Sinusoidal Waves on the Amino Acid Biosynthesis by Azobacter", *Z. Naturforsch*, 35, pp. 258-261 (1980).

Goodman, E.M. et al., "Effects of Electromagnetic Fields on Molecules and Cells", *International Review of Cytology*, 158, pp. 279-339 (1995).

Greenwalt, C.J. et al., "Kombucha, the fermented tea: Microbiology, composition, and claimed health effects," *Journal of Food Protection*, 63:976-981 (2000).

Grospietsch, T. et al., "Stimulating Effects of Modulated 150 MHz Electromagnetic Fields on the Growth of *Escherichia coli* in a Cavity Resonator", *Bioelectrochemistry and Bioenergetics*, 37, pp. 17-23 (1995).

Grundler W. et al., "Resonant-like dependence at yeast growth rate on microwave frequencies," *The British Journal of Cancer*, Supplement, England Mar. 1982, 45:206-208 (1982).

Grundler, W. et al., "Mechanisms of Electromagnetic Interaction with Cellular Systems", *Naturwissenschaften*, 79, pp. 551-559 (1992).

Grundler, W. et al., "Nonthermal Effects of Millimeter Microwaves on Yeast Growth", *Z. Naturforsch*, 33, pp. 15-22 (1978).

Ivaschuk, O.I. et al., "Exposure of Nerve Growth Factor-Treated PC12 Rat Pheochromocytoma Cells to a Modulated Radiofrequency Field at 836.55 MHz: Effects on c-*jun* and c-*fos* Expression", *Bioelectromagnetics*, 18, pp. 223-229 (1997).

Jelinek, F. et al., "Microelectronic Sensors for Measurement of Electromagnetic Fields of Living Cells and Experimental Results", *Bioelectrochemistry and Bioenergetics*, 48, pp. 261-266 (1999).

Lacy-Hulbert, A. et al., "Biological Responses to Electromagnetic Fields", *FASEB Journal*, 12, pp. 395-420 (1998).

Libertin, C.R. et al., "Effects of Gamma Rays, Ultraviolet Radiation, Sunlight, Microwaves and Electromagnetic Fields on Gene Expression Mediated by Human Immunodeficiency Virus Promoter", *Radiation Research*, 140, pp. 91-96 (1994).

Lin, H. et al., "Magnetic Field Activation of Protein-DNA Binding", *Journal of Cellular Biochemistry*, 70, pp. 297-303 (1998).

Lin, H. et al., "Specific Region of the c-*myc* Promoter Is Responsive to Electric and Magnetic Fields", *Journal of Cellular Biochemistry*, 54, pp. 281-288 (1994).

Liu C.H. et al., "The Isolation and identification of microbes from a fermented tea beverage, Haipao, and their interactions during Haipao fermentation," *Food Microbiology* (London), 13:407-415 (1996).

Loberg, L.I. et al., "Expression of Cancer-Related Genes in Human Cells Exposed to 60 Hz Magnetic Fields", *Radiation Research*, 153, pp. 679-684 (2000).

Mayser P. et al., "The yeast spectrum of the 'tea fungus Kombucha'," *Mycoses*, Blackwell, Berlin, Germany, 38:289-295 (1995).

Moore, R.L., "Biological Effects of Magnetic Fields: Studies with Microorganisms", *Canadian Journal of Microbiology*, 25, pp. 1145-1151 (1979).

Morehouse, C.A. et al., "Exposure of Daudi Cells to Low-Frequency Magnetic Fields Does Not Elevate MYC Steady-State mRNA Levels," *Radiation Research*, 153, pp. 663-669 (2000).

Norris, V. et al., "Do Bacteria Sing? Sonic Intercellular Communication Between Bacteria May Reflect Electromagnetic Intracellular Communication Involving Coherent Collective Vibrational Modes that Could Integrate Enzyme Activities and Gene Expression", *Molecular Microbiology*, 24, pp. 879-880 (1997).

Novelli, G. et al., "Study of the Effects on DNA of Electromagnetic Fields Using Clamped Homogeneous Electric Field Gel Electrophoresis", *Biomedicine & Pharmacotherapy*, 45, pp. 451-454 (1991).

Phillips, J.L., "Effects of Electromagnetic Field Exposure on Gene Transcription", *Journal of Cellular Biochemistry*, 51, pp. 381-386 (1993).

Pichko, V. B. et al., "Electromagnetic stimulation of productivity of microorganisms and its mechanisms", *Prikladnaya Biokhimiya I Mikrobiologiya*, 32(4): 468-472 (1996).

Ponne, C. T. et al., "Interaction of electromagnetic energy with biological material-relation to food processing", *Radiation Physics and Chemistry*, 45(4): 591-607 (1995).

Romano-Spica, V. et al., "Ets1 Oncogene Induction by ELF-Modulated 50 MHz Radiofrequency Electromagnetic Field", *Bioelectromagnetics*, 21, pp. 8-18 (2000).

Surawicz Christina M. et al., "The search for a better treatment for recurrent *Clostridium difficile* disease: Use of high-dose vancomycin combined with *Saccharomyces boulardii*," *Clinical Infectious Diseases*, 31:1012-1017 (2000).

Trosko, J.E., "Human Health Consequences of Environmentally-Modulated Gene Expression: Potential Roles of ELF-EMF Induced Epigenetic Versus Mutagenic Mechanisms of Disease", *Bioelectromagnetics*, 21, pp. 402-406 (2000).

Van den Bogaerde J. et al., "Immune sensitization to food, yeast and bacteria in Crohn's disease," *Alimentary Pharmacology & Therapeutics*, 15:1647-1653 (2001).

Van Rensburg, P. et al., "Engineering yeast for efficient cellulose degradation", *Yeast*, 14(1): 67-76 (1998).

Ventura, C. et al., "Elf-pulsed Magnetic Fields Modulate Opioid Peptide Gene Expression in Myocardial Cells", *Cardiovascular Research*, 45, pp. 1054-1064 (2000).

Woodward, A.M. et al., "Genetic Programming as an Analytical Tool for Non-linear Dielectric Spectroscopy", *Bioelectrochemistry and Bioenergetics*, 48, pp. 389-396 (1999).

Yonetani, T. et al., "Electromagnetic Properties of Hemoproteins", *The Journal of Biological Chemistry*, 247, pp. 2447-2455 (1972).

Zhang, L. et al., "Electrostimulation of the Dehydrogenase System of Yeast by Alternating Currents", *Bioelectrochemistry and Bioenergetics*, 28, pp. 341-353 (1992).

"*Saccharomyces cerevisiae* Meyen ex Hansen", China Catalogue of Cultures/China Committee of Culture Collection for Microorganisms (CCCCM), "www.im.ac.cn/database/YEAST/y122.html", Apr. 24, 1996, retrieved on Nov. 27, 2002.

U.S. Appl. No. 10/192,805, filed Nov. 29, 2004, Zhang.

U.S. Appl. No. 10/192,807, filed Nov. 29, 2004, Cheung.

Born et al., "The *Saccharomyces boulardii* Therapy of HIV-Associated Diarrhea", *Deutsche Medizinische Wochenschrift*, 118(20):765 (1993). (in German with English translation).

Dutta et al., *J. of Microwave Power*, vol. 14, No. 3, pp. 275-280 (1979).

Goodman, et al., "Magnetic Field Stress Induces Expression of HSP70", *Cell Stress & Chaperones* 3(2):79-88 (1998).

Grundler W., "Resonant Microwave Effect on Locally Fixed Yeast Microcolonies" *Z. Naturforsch* 44c:863-866 (1989).

Kim et al., "Anti-Sense and Anti-Fatigue Effects of Fermented Rice Bran", *Biosci Biotechnol Biochem.*, 65(10):2294-6 (2001).

Lin H. et al., "A Magnetic Field-Responsive Domain in the Human HSP70 Promoter", *J Cell Biochem*. 75:170-176 (1999).

Machado Caetano et al., "Immunopharmacological Effects of *Saccharomyces boulardii* in Healthy Human Volunteers", *Int'l Immunology and Immunopathology*, 8(3):245-259 (1986).

Ortuno et al., "Oral Administration of Yeast, *Saccharomyces cerevisiae*, Enhances the Cellular Innate Immune response of Gilthead seabream (*Sparus aurata* L.)", *Vet Immunol Immunopathol*, 85(1-2):41-50 (2002).

Peret Filho et al., "Dose Effect of Oral *Saccharomyces boulardii* Treatment on Morbidity and Mortality in Immunosuppressed Mice", *J Med Microbiol.*, 47(2):111-6 (1998).

Saha et al., "Microbial Manipulation of Rumen Fermentation Using *Saccharomyces cerevisiae* as Probiotics", *Current Science* (Bangalore), 77(5):696-697 (1999).

WHO World Health Organization; WebPages http:www.who.int/peh/emf/about/WhatisEMF/en/ and http:www.who.int/peh-emf/about/WhatisEMF/en/index3.html retrieved Jun. 10, 2004.

* cited by examiner

METHODS AND COMPOSITIONS FOR TREATING MALE SEXUAL DYSFUNCTION

FIELD OF THE INVENTION

The invention relates to compositions that can ameliorate or prevent sexual disorders and are useful as a dietary supplement or medication. These compositions contain yeast cells obtainable by growth in electromagnetic fields with specific frequencies and field strengths.

BACKGROUND OF THE INVENTION

Impotence is one of the most common forms of male sexual dysfunction. It may be caused by diseases (e.g., diabetes) or certain medications. A variety of Western medicines and Chinese herbal medicines have been used to restore erectile function. However, these medicines are all less than satisfactory. There remains a need for an effective method for treating impotence.

SUMMARY OF THE INVENTION

This invention is based on the discovery that certain yeast cells can be activated by electromagnetic fields having specific frequencies and field strengths to treat sexual disorders. Compositions comprising these activated yeast cells can be used as a dietary supplement for improving sexual functions, e.g., for alleviating or preventing impotence.

This invention embraces a composition comprising a plurality of yeast cells that have been cultured in an alternating electric field having a frequency in the range of about 7900–13200 MHz (e.g., 7900–8000 or 12700–13200), and a field intensity in the range of about 240–500 mV/cm (e.g., 260–280, 290–320, 300–320, 310–340, 330–360, 350–380, 360–400, or 420–460 mV/cm). The yeast cells are cultured in the alternating electric field for a period of time sufficient to substantially increase the capability of said plurality of yeast cells to produce substances for treating sexual disorders (e.g., impotence). In one embodiment, the frequency and/or the field strength of the alternating electric field can be altered within the aforementioned ranges during said period of time. In other words, the yeast cells can be exposed to a series of electromagnetic fields. An exemplary period of time is about 40–180 hours (e.g., 60–168 hours).

Also included in this invention is a composition comprising a plurality of yeast cells that have been cultured under acidic conditions in an alternating electric field having a frequency in the range of about 12700–13200 MHz (e.g., 13000–13200 MHz) and a field strength in the range of about 240 to 420 mV/cm (e.g., 260–280 or 360–390 mV/cm). In one embodiment, the yeast cells are exposed to a series of electromagnetic fields. An exemplary period of time is about 30–100 hours (e.g., 35–60 hours).

Included in this invention are also methods of making the above compositions.

Yeast cells that can be included in this composition can be derived from parent strains publically available from the China General Microbiological Culture Collection Center ("CGMCC"), China Committee for Culture Collection of Microorganisms, Institute of Microbiology, Chinese Academy of Sciences, Haidian, P.O. BOX 2714, Beijing, 100080, China. Useful yeast species include, but are not limited to, *Saccharomyces cerevisiae*, *Saccharomyces carlsbergensis*, *Saccharomyces rouxii*, *Saccharomyces sake*, *Saccharomyces uvarum*, *Saccharomyces* sp., *Schizosaccharomyces pombe*, and *Rhodotorula aurantiaca*. For instance, the yeast cells can be of the strain *Saccharomyces cerevisiae* Hansen AS2.502 or AS2.69, *Saccharomyces* sp. AS2.3 11, *Schizosaccharomyces pombe* Lindner AS2.994, *Saccharomyces sake* Yabe ACCC2045, *Saccharomyces uvarum* Beijer IFFI1044, *Saccharomyces rouxii* Boutroux AS2.180, *Saccharomyces cerevisiae* Hansen Var. ellipsoideus AS2.612, *Saccharomyces carlsbergensis* Hansen AS2.377, or *Rhodotorula rubar* (Demme) Lodder AS2.282. Other useful yeast strains are illustrated in Table 1.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting. Throughout this specification and claims, the word "comprise," or variations such as "comprises" or "comprising" will be understood to imply the inclusion of a stated integer or group of integers but not the exclusion of any other integer or group of integers.

Other features and advantages of the invention will be apparent from the following detailed description, and from the claims.

DETAILED DESCRIPTION OF THE INVENTION

Figure 1:
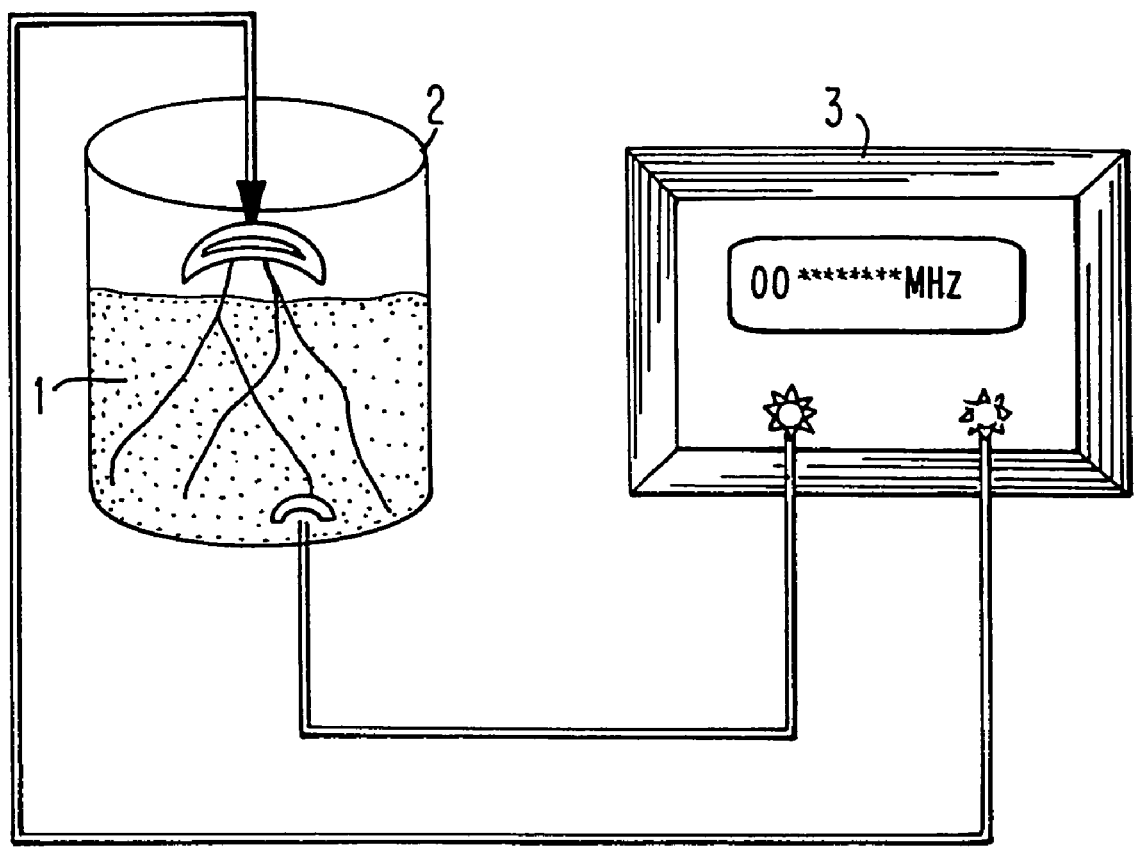
FIG. 1 is a schematic diagram showing an exemplary apparatus for activating yeast cells using electromagnetic fields. 1: yeast culture; 2: container; 3: power supply.

This invention is based on the discovery that certain yeast strains can be activated by electromagnetic fields ("EMF") having specific frequencies and field strengths to produce agents useful in treating sexual disorders, e.g., impotence. Yeast compositions containing activated yeast cells can be used as medication, or as a dietary supplement in the form of health drinks or dietary pills.

In certain embodiments, the yeast compositions of this invention stimulate the secretion of male hormones, e.g., testosterone. In other embodiments, the yeast compositions decrease or inhibit the effects of certain chemicals/drugs in the body that contribute to male sexual dysfunction (e.g., impotence). In further embodiments, the yeast compositions alleviate male sexual dysfunction (e.g., impotence) caused by diabetes.

Since the activated yeast cells contained in these yeast compositions have been cultured to endure acidic conditions (pH 2.5–4.2), the compositions are stable in the stomach and can pass on to the intestines. Once in the intestines, the yeast cells are ruptured by various digestive enzymes, and the bioactive agents are released and readily absorbed.

I. Yeast Strains Useful in the Invention

The types of yeasts useful in this invention include, but are not limited to, yeasts of the genera of *Saccharomyces, Rhodotorula*, and *Schizosaccharomyces*.

Exemplary species within the above-listed genera include, but are not limited to, the species illustrated in Table 1. Yeast strains useful in this invention can be obtained from laboratory cultures, or from publically accessible culture depositories, such as CGMCC and the American Type Culture Collection, 10801 University Boulevard, Manassas, Va. 20110-2209. Non-limiting examples of useful strains (with the accession numbers of CGMCC) are *Saccharomyces cerevisiae* Hansen AS2.502 and AS2.69, *Saccharomyces* sp. AS2.311, *Schizosaccharomyces pombe* Lindner AS2.994, *Saccharomyces sake* Yabe ACCC2045, *Saccharomyces uvarum* Beijer IFFI1044, *Saccharomyces rouxii* Boutroux AS2.180, *Saccharomyces cerevisiae* Hansen Var. ellipsoideus AS2.612, *Saccharomyces carlsbergensis* Hansen AS2.377, and *Rhodotorula rubar* (Demme) Lodder AS2.282. Other non-limiting examples of useful strains are listed in Table 1. In general, yeast strains preferred in this invention are those used for fermentation in the food and wine industries. As a result, compositions containing these yeast cells are safe for human consumption.

The preparation of the yeast compositions of this invention is not limited to starting with a pure strain of yeast. A yeast composition of the invention may be produced by culturing a mixture of yeast cells of different species or strains.

TABLE 1

Exemplary Yeast Strains

*Saccharomyces cerevisiae* Hansen

| | | | | |
|---|---|---|---|---|
| ACCC2034 | ACCC2035 | ACCC2036 | ACCC2037 | ACCC2038 |
| ACCC2039 | ACCC2040 | ACCC2041 | ACCC2042 | AS2. 1 |
| AS2. 4 | AS2. 11 | AS2. 14 | AS2. 16 | AS2. 56 |
| AS2. 69 | AS2. 70 | AS2. 93 | AS2. 98 | AS2. 101 |
| AS2. 109 | AS2. 110 | AS2. 112 | AS2. 139 | AS2. 173 |
| AS2. 174 | AS2. 182 | AS2. 196 | AS2. 242 | AS2. 336 |
| AS2. 346 | AS2. 369 | AS2. 374 | AS2. 375 | AS2. 379 |
| AS2. 380 | AS2. 382 | AS2. 390 | AS2. 393 | AS2. 395 |
| AS2. 396 | AS2. 397 | AS2. 398 | AS2. 399 | AS2. 400 |
| AS2. 406 | AS2. 408 | AS2. 409 | AS2. 413 | AS2. 414 |
| AS2. 415 | AS2. 416 | AS2. 422 | AS2. 423 | AS2. 430 |
| AS2. 431 | AS2. 432 | AS2. 451 | AS2. 452 | AS2. 453 |
| AS2. 458 | AS2. 460 | AS2. 463 | AS2. 467 | AS2. 486 |
| AS2. 501 | AS2. 502 | AS2. 503 | AS2. 504 | AS2. 516 |
| AS2. 535 | AS2. 536 | AS2. 558 | AS2. 560 | AS2. 561 |
| AS2. 562 | AS2. 576 | AS2. 593 | AS2. 594 | AS2. 614 |
| AS2. 620 | AS2. 628 | AS2. 631 | AS2. 666 | AS2. 982 |
| AS2. 1190 | AS2. 1364 | AS2. 1396 | IFFI1001 | IFFI1002 |
| IFFI1005 | IFFI1006 | IFFI1008 | IFFI1009 | IFFI1010 |
| IFFI1012 | IFFI1021 | IFFI1027 | IFFI1037 | IFFI1042 |
| IFFI1043 | IFFI1045 | IFFI1048 | IFFI1049 | IFFI1050 |
| IFFI1052 | IFFI1059 | IFFI1060 | IFFI1062 | IFFI1063 |
| IFFI1202 | IFFI1203 | IFFI1206 | IFFI1209 | IFFI1210 |
| IFFI1211 | IFFI1212 | IFFI1213 | IFFI1214 | IFFI1215 |
| IFFI1220 | IFFI1221 | IFFI1224 | IFFI1247 | IFFI1248 |
| IFFI1251 | IFFI1270 | IFFI1277 | IFFI1287 | IFFI1289 |
| IFFI1290 | IFFI1291 | IFFI1292 | IFFI1293 | IFFI1297 |
| IFFI1300 | IFFI1301 | IFFI1302 | IFFI1307 | IFFI1308 |
| IFFI1309 | IFFI1310 | IFFI1311 | IFFI1331 | IFFI1335 |
| IFFI1336 | IFFI1337 | IFFI1338 | IFFI1339 | IFFI1340 |
| IFFI1345 | IFFI1348 | IFFI1396 | IFFI1397 | IFFI1399 |
| IFFI1411 | IFFI1413 | IFFI1441 | IFFI1443 | |

*Saccharomyces cerevisiae* Hansen Var. *ellipsoideus* (Hansen) Dekker

| | | | | |
|---|---|---|---|---|
| ACCC2043 | AS2.2 | AS2.3 | AS2.8 | AS2.53 |
| AS2.163 | AS2.168 | AS2.483 | AS2.541 | AS2.559 |
| AS2.606 | AS2.607 | AS2.611 | AS2.612 | |

*Saccharomyces chevalieri* Guilliermond

| | |
|---|---|
| AS2.131 | AS2.213 |

*Saccharomyces delbrueckii*

AS2.285

*Saccharomyces delbrueckii* Lindner ver. *mongolicus* (Saito) Lodder et van Rij

| | |
|---|---|
| AS2.209 | AS2.1157 |

*Saccharomyces exiguous* Hansen

| | |
|---|---|
| AS2.349 | AS2.1158 |

*Saccharomyces fermentati* (Saito) Lodder et van Rij

| | |
|---|---|
| AS2.286 | AS2.343 |

*Saccharomyces logos* van laer et Denamur ex Jorgensen

| | | |
|---|---|---|
| AS2.156 | AS2.327 | AS2.335 |

TABLE 1-continued

Exemplary Yeast Strains

*Saccharomyces mellis* (Fabian et Quinet) Lodder et kreger van Rij

AS2.195

*Saccharomyces mellis Microellipsoides* Osterwalder

AS2.699

*Saccharomyces oviformis* Osteralder

AS2.100

*Saccharomyces rosei* (Guilliermond) Lodder et Kreger van Rij

AS2.287

*Saccharomyces rouxii* Boutroux

| AS2.178 | AS2.180 | AS2.370 | AS2.371 | |

*Saccharomyces sake* Yabe

ACCC2045

*Candida arborea*

AS2.566

*Candida lambica* (Lindner et Genoud) van. Uden et Buckley

AS2.1182

*Candida krusei* (Castellani) Berkhout

AS2.1045

*Candida lipolytica* (Harrison) Diddens et Lodder

| AS2.1207 | AS2.1216 | AS2.1220 | AS2.1379 | AS2.1398 |
| AS2.1399 | AS2.1400 | | | |

*Candida parapsilosis* (Ashford) Langeron et Talice Var. *intermedia* Van Rij et Verona

AS2.491

*Candida parapsilosis* (Ashford) Langeron et Talice

AS2.590

*Candida pulcherrima* (Lindner) Windisch

AS2.492

*Candida rugousa* (Anderson) Diddens et Lodder

| AS2.511 | AS2.1367 | AS2.1369 | AS2.1372 | AS2.1373 |
| AS2.1377 | AS2.1378 | AS2.1384 | | |

*Candida tropicalis* (Castellani) Berkhout

| ACCC2004 | ACCC2005 | ACCC2006 | AS2.164 | AS2.402 |
| AS2.564 | AS2.565 | AS2.567 | AS2.568 | AS2.617 |
| AS2.637 | AS2.1387 | AS2.1397 | | |

*Candida utilis* Henneberg Lodder et Kreger Van Rij

| AS2.120 | AS2.281 | AS2.1180 | | |

*Crebrothecium ashbyii* (Guilliermond)
Routein (*Eremothecium ashbyii* Guilliermond)

| AS2.481 | AS2.482 | AS2.1197 | | |

*Geotrichum candidum* Link

| ACCC2016 | AS2.361 | AS2.498 | AS2.616 | AS2.1035 |
| AS2.1062 | AS2.1080 | AS2.1132 | AS2.1175 | AS2.1183 |

*Hansenula anomala* (Hansen)H et P sydow

| ACCC2018 | AS2.294 | AS2.295 | AS2.296 | AS2.297 |
| AS2.298 | AS2.299 | AS2.300 | AS2.302 | AS2.338 |
| AS2.339 | AS2.340 | AS2.341 | AS2.470 | AS2.592 |
| AS2.641 | AS2.642 | AS2.782 | AS2.635 | AS2.794 |

*Hansenula arabitolgens* Fang

AS2.887

*Hansenula jadinii* (A. et R Sartory Weill et Meyer) Wickerham

ACCC2019

*Hansenula saturnus* (Klocker) H et P sydow

ACCC2020

TABLE 1-continued

Exemplary Yeast Strains

*Hansenula schneggii* (Weber) Dekker

AS2.304

*Hansenula subpelliculosa* Bedford

| AS2.740 | AS2.760 | AS2.761 | AS2.770 | AS2.783 |
| AS2.790 | AS2.798 | AS2.866 | | |

*Kloeckera apiculata* (Reess emend. Klocker) Janke

| ACCC2022 | ACCC2023 | AS2.197 | AS2.496 | AS2.714 |
| ACCC2021 | AS2.711 | | | |

*Lipomycess starkeyi* Lodder et van Rij

| AS2.1390 | ACCC2024 | | | |

*Pichia farinosa* (Lindner) Hansen

| ACCC2025 | ACCC2026 | AS2.86 | AS2.87 | AS2.705 |
| AS2.803 | | | | |

*Pichia membranaefaciens* Hansen

| ACCC2027 | AS2.89 | AS2.661 | AS2.1039 | |

*Rhodosporidium toruloides* Banno

ACCC2028

*Rhodotorula glutinis* (Fresenius) Harrison

| AS2.2029 | AS2.280 | ACCC2030 | AS2.102 | AS2.107 |
| AS2.278 | AS2.499 | AS2.694 | AS2.703 | AS2.704 |
| AS2.1146 | | | | |

*Rhodotorula minuta* (Saito) Harrison

AS2.277

*Rhodotorula rubar* (Demme) Lodder

| AS2.21 | AS2.22 | AS2.103 | AS2.105 | AS2.108 |
| AS2.140 | AS2.166 | AS2.167 | AS2.272 | AS2.279 |
| AS2.282 | ACCC2031 | | | |

*Rhodotorula aurantiaca* (Saito) Lodder

| AS2.102 | AS2.107 | AS2.278 | AS2.499 | AS2.694 |
| AS2.703 | AS2.1146 | | | |

*Saccharomyces carlsbergensis* Hansen

| AS2.113 | ACCC2032 | ACCC2033 | AS2.312 | AS2.116 |
| AS2.118 | AS2.121 | AS2.132 | AS2.162 | AS2.189 |
| AS2.200 | AS2.216 | AS2.265 | AS2.377 | AS2.417 |
| AS2.420 | AS2.440 | AS2.441 | AS2.443 | AS2.444 |
| AS2.459 | AS2.595 | AS2.605 | AS2.638 | AS2.742 |
| AS2.745 | AS2.748 | AS2.1042 | | |

*Saccharomyces uvarum* Beijer

| IFFI1023 | IFFI1032 | IFFI1036 | IFFI1044 | IFFI1072 |
| IFFI1205 | IFFI1207 | | | |

*Saccharomyces willianus* Saccardo

| AS2.5 AS2.7 | AS2.119 | AS2.152 | AS2.293 | |
| AS2.381 | AS2.392 | AS2.434 | AS2.614 | AS2.1189 |

*Saccharomyces* sp.

AS2.311

*Saccharomycodes ludwigii* Hansen

| ACCC2044 | AS2.243 | AS2.508 | | |

*Saccharomycodes sinenses* Yue

AS2.1395

*Schizosaccharomyces octosporus* Beijerinck

| ACCC2046 | AS2.1148 | | | |

*Schizosaccharomyces pombe* Lindner

| ACCC2047 | ACCC2048 | AS2.214 | AS2.248 | AS2.249 |
| AS2.255 | AS2.257 | AS2.259 | AS2.260 | AS2.274 |
| AS2.994 | AS2.1043 | AS2.1149 | AS2.1178 | IFFI1056 |

*Sporobolomyces roseus* Kluyver et van Niel

| ACCC2049 | ACCC2050 | AS2.19 | AS2.962 | AS2.1036 |

TABLE 1-continued

Exemplary Yeast Strains

| | | | |
|---|---|---|---|
| ACCC2051 | AS2.261 | AS2.262 | |
| | *Torulopsis candida* (Saito) Lodder | | |
| AS2.270 | ACCC2052 | | |
| | *Torulopsis famta* (Harrison) Lodder et van Rij | | |
| ACCC2053 | AS2.685 | | |
| | *Torulopsis globosa* (Olson et Hammer) Lodder et van Rij | | |
| ACCC2054 | AS2.202 | | |
| | *Torulopsis inconspicua* Lodder et Kreger van Rij | | |
| AS2.75 | | | |
| | *Trichosporon behrendii* Lodder et Kreger van Rij | | |
| ACCC2056 | AS2.1193 | | |
| | *Trichosporon capitatum* Diddens et Lodder | | |
| ACCC2056 | AS2.1385 | | |
| | *Trichosporon cutaneum* (de Beurm et al.) Ota | | |
| ACCC2057 | AS2.25 | AS2.570 | AS2.571 | AS2.1374 |
| | *Wickerhamia fluorescens* (Soneda) Soneda | | |
| ACCC2058 | AS2.1388 | | |

II. Application of Electromagnetic Fields

An electromagnetic field useful in this invention can be generated and applied by various means well known in the art. For instance, the EMF can be generated by applying an alternating electric field or an oscillating magnetic field.

Alternating electric fields can be applied to cell cultures through electrodes in direct contact with the culture medium, or through electromagnetic induction. See, e.g., FIG. 1. Relatively high electric fields in the medium can be generated using a method in which the electrodes are in contact with the medium. Care must be taken to prevent electrolysis at the electrodes from introducing undesired ions into the culture and to prevent contact resistance, bubbles, or other features of electrolysis from dropping the field level below that intended. Electrodes should be matched to their environment, for example, using Ag—AgCl electrodes in solutions rich in chloride ions, and run at as low a voltage as possible. For general review, see Goodman et al., *Effects of EMF on Molecules and Cells*, International Review of Cytology, A Survey of Cell Biology, Vol. 158, Academic Press, 1995.

The EMFs useful in this invention can also be generated by applying an oscillating magnetic field. An oscillating magnetic field can be generated by oscillating electric currents going through Helmholtz coils. Such a magnetic field in turn induces an electric field.

The frequencies of EMFs useful in this invention range from about 7900 MHz to 13200 MHz (e.g., 7900–8000 or 12700–13200). Exemplary frequencies include 7963, 7975, 12744, 13092, and 13123 MHz. The field strength of the electric field useful in this invention ranges from about 240–500 mV/cm (e.g., 260–280, 290–320, 300–320, 310–340, 330–360, 350–380, 360–390, or 420–460 mV/cm). Exemplary field strengths include 266, 272, 307, 318, 322, 343, 348, 367, 375, 397, and 438 mV/cm.

When a series of EMFs are applied to a yeast culture, the yeast culture can remain in the same container while the same set of EMF generator and emitters is used to change the frequency and/or field strength. The EMFs in the series can each have a different frequency or a different field strength; or a different frequency and a different field strength. Such frequencies and field strengths are preferably within the above-described ranges. Although any practical number of EMFs can be used in a series, it may be preferred that the yeast culture be exposed to a total of 2, 3, 4, 5, 6, 7, 8, 9, 10, 11, 12, 13, or more EMFs in a series. In one embodiment, the yeast culture is exposed to a series of EMFs, wherein the frequency of the electric field is alternated in the range of about 7900–8000, 12700–12800, and 13050–13200 MHz.

Although the yeast cells can be activated after even a few hours of culturing in the presence of an EMF, it may be preferred that the activated yeast cells be allowed to multiply and grow in the presence of the EMF(s) for a total of 40–180 hours.

FIG. 1 illustrates an exemplary apparatus for generating alternating electric fields. An electric field of a desired frequency and intensity can be generated by an AC source (3) capable of generating an alternating electric field, preferably in a sinusoidal wave form, in the frequency range of 5 to 20,000 MHz. Signal generators capable of generating signals with a narrower frequency range can also be used. If desired, a signal amplifier can also be used to increase the output. The culture container (2) can be made from a non-conductive material, e.g., glass, plastic or ceramic. The cable connecting the culture container (2) and the signal generator (3) is preferably a high frequency coaxial cable with a transmission frequency of at least 30 GHz.

The alternating electric field can be applied to the culture by a variety of means, including placing the yeast culture (1) in close proximity to the signal emitters such as a metal wire or tube capable of transmitting EMFs. The metal wire or tube can be made of red copper, and be placed inside the container (2), reaching as deep as 3–30 cm. For example, if the fluid in the container (2) has a depth of 15–20 cm, 20–30 cm, 30–50 cm, 50–70 cm, 70–100 cm, 100–150 cm or 150–200 cm, the metal wire can be 3–5 cm, 5–7 cm, 7–10 cm, 10–15 cm, 15–20 cm, 20–30 cm, and 25–30 cm from the bottom of the container (2), respectively. The number of metal wires/tubes used can be from 1 to 10 (e.g., 2 to 3). It is recommended, though not mandated, that for a culture having a volume up to 10 L, metal wires/tubes having a diameter of 0.5 to 2 mm be used. For a culture having a volume of 10–100 L, metal wires/tubes having a diameter of 3 to 5 mm can be used. For a culture having a volume of 100–1000 L, metal wires/tubes having a diameter of 6 to 15 mm can be used. For a culture having a volume greater than 1000 L, metal wires/tubes having a diameter of 20–25 mm can be used.

In one embodiment, the electric field is applied by electrodes submerged in the culture (1). In this embodiment, one of the electrodes can be a metal plate placed on the bottom of the container (2), and the other electrode can comprise a plurality of electrode wires evenly distributed in the culture (1) so as to achieve even distribution of the electric field energy.

III. Culture Media

Culture media useful in this invention contain sources of nutrients that can be assimilated by yeast cells. Complex carbon-containing substances in a suitable form (e.g., carbohydrates such as sucrose, glucose, dextrose, maltose, xylose, cellulose, starch, etc.) can be the carbon sources for yeast cells. The exact quantity of the carbon sources can be adjusted in accordance with the other ingredients of the medium. In general, the amount of carbohydrates varies between about 1% and 10% by weight of the medium and preferably between about 1% and 5%, and most preferably about 2%. These carbon sources can be used individually or in combination. Amino acid-containing substances such as beef extract and peptone can also be added. In general, the amount of amino acid containing substances varies between about 0.1% and 1% by weight of the medium and preferably between about 0.1% and 0.5%. Among the inorganic salts which can be added to a culture medium are the customary salts capable of yielding sodium, potassium, calcium, phosphate, sulfate, carbonate, and like ions. Non-limiting examples of nutrient inorganic salts are $(NH_4)_2HPO_4$, $CaCO_3$, $KH_2PO_4$, $K_2HPO_4$, $MgSO_4$, $NaCl$, and $CaSO_4$.

IV. Electromagnetic Activation of Yeast Cells

To activate or enhance the ability of yeast cells to produce agents useful for treating sexual disorders (e.g., impotence), these cells can be cultured in an appropriate medium under sterile conditions at 20–35° C. (e.g., 28–32° C.) for a sufficient amount of time (e.g., 60–168 hours) in an alternating electric field or a series of alternating electric fields as described above.

An exemplary set-up of the culture process is depicted in FIG. 1 (see above). An exemplary culture medium contains the following per 950 ml of sterilized water: 6 g of sucrose, 12 g of mannitol, 90 µg of Vitamin D, 60 µg of Vitamin E, 40 µg of Vitamin H, 60 mg of Vitamin $B_6$, 50 ml of fetal bovine serum, 0.2 g of $KH_2PO_4$, 0.25 g of $MgSO_4 \cdot 7H_2O$, 0.3 g of NaCl, 0.2 g of $CaSO_4 \cdot 2H_2O$, 4 g of $CaCO_3 \cdot 5H_2O$, and 2.5 g of peptone. Yeast cells of the desired strain(s) are then added to the culture medium to form a mixture containing $1 \times 10^8$ cells per 1000 ml of culture medium. The yeast cells can be of any of the strains listed in Table 1. The mixture is then added to the apparatus shown in FIG. 1.

The activation process of the yeast cells involves the following steps: (1) maintaining the temperature of the activation apparatus at 24–33° C. (e.g., 28–32° C.), and culturing the yeast cells for 24–30 hours (e.g., 28 hours); (2) applying an alternating electric field having a frequency of 7963 MHz and a field strength of 260–280 mV/cm (e.g., 272 mV/cm) for 12–18 hours (e.g., 16 hours); (3) then applying an alternating electric field having a frequency of 7975 MHz and a field strength of 310–340 mV/cm (e.g., 322 mV/cm) for 32–38 hours (e.g., 36 hours); (4) then applying an alternating electric field having a frequency of 12744 MHz and a field strength of 330–360 mV/cm (e.g., 343 mV/cm) for 32–38 hours (e.g., 36 hours); (5) then applying an alternating electric field having a frequency of 13092 MHz and a field strength of 350–380 mV/cm (e.g., 367 mV/cm) for 32–38 hours (e.g., 36 hours); and (6) then applying an alternating electric field having a frequency of 13123 MHz and a field strength of 290–320 mV/cm (e.g., 307 mV/cm) for 12–18 hours (e.g., 16 hours). The activated yeast cells are then recovered from the culture medium by various methods known in the art, dried (e.g., by lyophilization) and stored at 4° C. Preferably, the concentration of the dried yeast cells is no less than $10^{10}$ cells/g.

V. Acclimatization of Yeast Cells To the Gastric Environment

Because the yeast compositions of this invention must pass through the stomach before reaching the small intestine, where the effective components are released from these yeast cells, it is preferred that these yeast cells be cultured under acidic conditions to acclimatize the cells to the gastric juice. This acclimatization process results in better viability of the yeast cells in the acidic gastric environment.

To achieve this, the yeast powder containing activated yeast cells can be mixed with a highly acidic acclimatizing culture medium at 10 g (containing more than $10^{10}$ activated cells per gram) per 1000 ml. The yeast mixture is then cultured first in the presence of an alternating electric field having a frequency of 13092 MHz and a field strength of 360–390 mV/cm (e.g., 375 mV/cm) at about 28 to 32° C. for 32 to 42 hours (e.g., 36 hours). The resultant yeast cells can then be further incubated in the presence of an alternating electric field having a frequency of 13123 MHz and a field strength of 260–280 mV/cm (e.g., 266 mV/cm) at about 28 to 32° C. for 16 to 28 hours (e.g., 20 hours). The resulting acclimatized yeast cells are then dried and stored either in powder form ($\geq 10^{10}$ cells/g) at room temperature or in vacuum at 0–4° C.

An exemplary acclimatizing culture medium is made by mixing 700 ml fresh pig gastric juice and 300 ml wild Chinese hawthorn extract. The pH of the acclimatizing culture medium is adjusted to 2.5 with 0.1 M hydrochloric acid (HCl) and/or 0.2 M potassium hydrogen phthalate ($C_6H_4(COOK)COOH$). The fresh pig gastric juice is prepared as follows. At about 4 months of age, newborn Holland white pigs are sacrificed, and the entire contents of their stomachs are retrieved and mixed with 2000 ml of water under sterile conditions. The mixture is then allowed to stand for 6 hours at 4° C. under sterile conditions to precipitate food debris. The supernatant is collected for use in the acclimatizing culture medium. To prepare the wild Chinese hawthorn extract, 500 g of fresh wild Chinese hawthorn is dried under sterile conditions to reduce water content ($\leq 8\%$). The dried fruit is then ground ($\geq 20$ mesh) and added to 1500 ml of sterilized water. The hawthorn slurry is allowed to stand for 6 hours at 4° C. under sterile conditions. The hawthorn supernatant is collected to be used in the acclimatizing culture medium.

VI. Manufacture of Yeast Compositions

Figure 2:
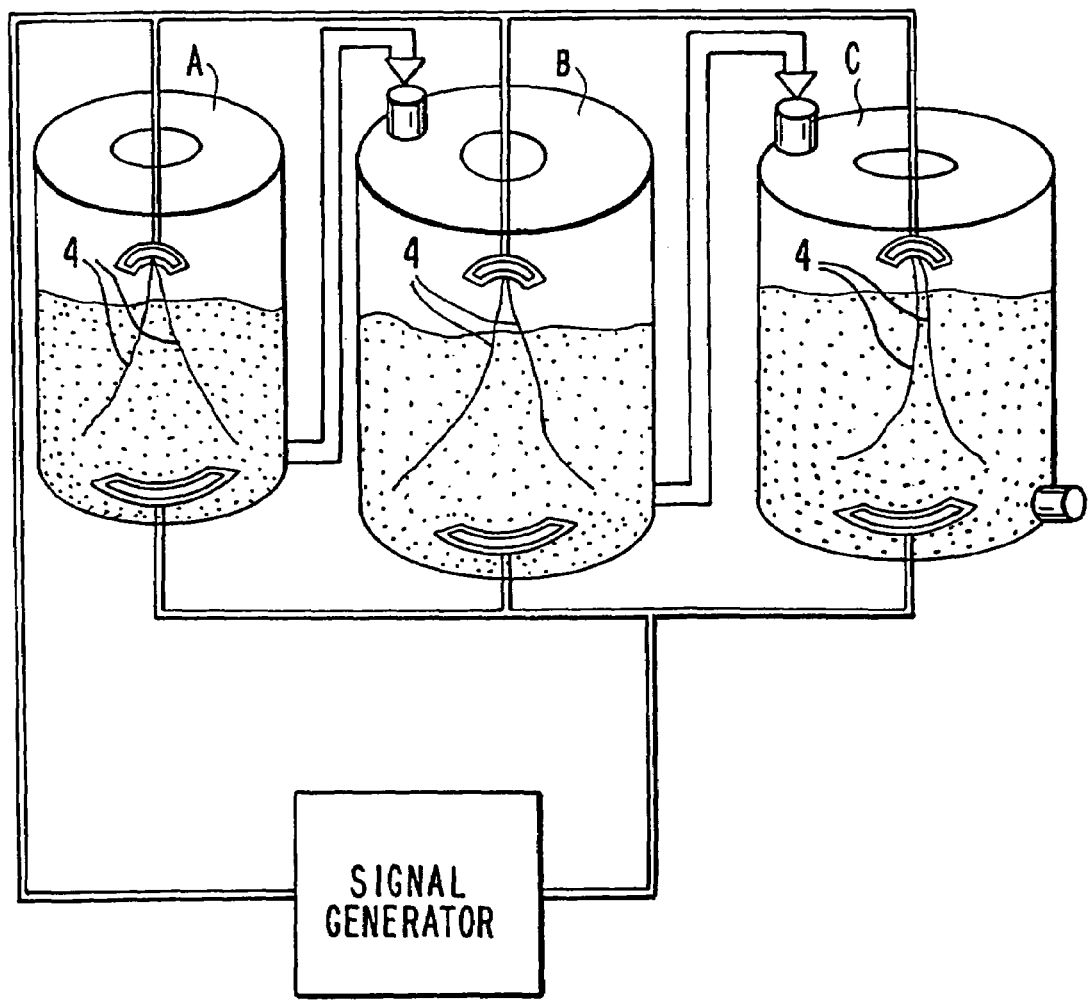
FIG. 2 is a schematic diagram showing an exemplary apparatus for making yeast compositions of the invention. The apparatus comprises a signal generator (such as models 83721B and 83741A manufactured by HP) and interconnected containers A, B and C.

To manufacture the yeast compositions of the invention, an apparatus depicted in FIG. 2 or an equivalent thereof can be used. This apparatus includes three containers, a first container (A), a second container (B), and a third container (C), each equipped with a pair of electrodes (4). One of the electrodes is a metal plate placed on the bottom of the containers, and the other electrode comprises a plurality of electrode wires evenly distributed in the space within the container to achieve even distribution of the electric field energy. All three pairs of electrodes are connected to a common signal generator.

The culture medium used for this purpose is a mixed fruit extract solution containing the following ingredients per 1000 L: 300 L of wild Chinese hawthorn extract, 300 L of jujube extract, 300 L of Wu Wei Zi (*Schisandra chinensis* (Turez) Baill seeds) extract, and 100 L of soy bean extract. To prepare hawthorn, jujube and Wu Wei Zi extracts, the fresh fruits are washed and dried under sterile conditions to reduce the water content to no higher than 8%. One hundred kilograms of the dried fruits are then ground ($\geqq 20$ mesh) and added to 400 L of sterilized water. The mixtures are stirred under sterile conditions at room temperature for twelve hours, and then centrifuged at 1000 rpm to remove insoluble residues. To make the soy bean extract, fresh soy beans are washed and dried under sterile conditions to reduce the water content to no higher than 8%. Thirty kilograms of dried soy beans are then ground into particles of no smaller than 20 mesh, and added to 130 L of sterilized water. The mixture is stirred under sterile conditions at room temperature for twelve hours and centrifuged at 1000 rpm to remove insoluble residues. To make the culture medium, these ingredients are mixed according to the above recipe, and the mixture is autoclaved at 121° C. for 30 minutes and cooled to below 40° C. before use.

One thousand grams of the activated yeast powder prepared as described above (Section V, supra) is added to 1000 L of the mixed fruit extract solution, and the yeast solution is transferred to the first container (A) shown in FIG. 2. The yeast cells are then cultured in the presence of an alternating electric field having a frequency of 13092 MHz and a field strength of about 300–420 mV/cm (e.g., 397 mV/cm) at 28–32° C. under sterile conditions for 36 hours. The yeast cells are further incubated in an alternating electric field having a frequency of 13123 MHz and a field strength of 310–330 mV/cm (e.g., 322 mV/cm). The culturing continues for another 12 hours.

The yeast culture is then transferred from the first container (A) to the second container (B) which contains 1000 L of culture medium (if need be, a new batch of yeast culture can be started in the now available first container (A)), and subjected to an alternating electric field having a frequency of 13092 MHz and a field strength of 420–460 mV/cm (e.g., 438 mV/cm) for 24 hours. Subsequently the frequency and field strength of the electric field are changed to 13123 MHz and 330–360 mV/cm (e.g., 348 mV/cm), respectively. The culturing continues for another 12 hours.

The yeast culture is then transferred from the second container (B) to the third container (C) which contains 1000 L of culture medium, and subjected to an alternating electric field having a frequency of 13092 MHz and a field strength of 310–340 mV/cm (e.g., 318 mV/cm) for 24 hours. Subsequently the frequency and field strength of the electric field are changed to 13123 MHz and 260–280 mV/cm (e.g., 272 mV/cm), respectively. The culturing continues for another 12 hours.

The yeast culture from the third container (C) can then be packaged into vacuum sealed bottles for use as dietary supplement, e.g., health drinks, or medication in the form of pills, powder, etc. If desired, the final yeast culture can also be dried within 24 hours and stored in powder form. The dietary supplement can be taken three to four times daily at 30–60 ml per dose for a three-month period, preferably 10–30 minutes before meals and at bedtime.

In some embodiments, the compositions of the invention can also be administered intravenously or peritoneally in the form of a sterile injectable preparation. Such a sterile preparation can be prepared as follows. A sterilized health drink composition is first treated under ultrasound (20,000 Hz) for 10 minutes and then centrifuged for another 10 minutes. The resulting supernatant is adjusted to pH 7.2–7.4 using 1 M NaOH and subsequently filtered through a membrane (0.22 μm for intravenous injection and 0.45 μm for peritoneal injection) under sterile conditions. The resulting sterile preparation is submerged in a 35–38° C. water bath for 30 minutes before use. In other embodiments, the compositions of the invention may also be formulated with pharmaceutically acceptable carriers to be orally administered in any orally acceptable dosage form including, but not limited to, capsules, tablets, suspensions or solutions.

The yeast compositions of the present invention are derived from yeasts used in food and pharmaceutical industries. The yeast compositions are thus devoid of side effects associated with many pharmaceutical compounds.

VII. EXAMPLES

The following examples are meant to illustrate the methods and materials of the present invention. Suitable modifications and adaptations of the described conditions and parameters which are obvious to those skilled in the art are within the spirit and scope of the present invention.

The activated yeast compositions used in the following experiments were prepared as described above, using *Saccharomyces cerevisiae* Hansen AS2.502 cells cultured in the presence of an alternating electric field having the electric field frequency and field strength exemplified in the parentheses following the recommended ranges listed in Section IV, supra. Control yeast compositions were those prepared in the same manner except that the yeast cells were cultured in the absence of EMFs. Unless otherwise indicated, the yeast compositions and the corresponding controls were administered to the animals by intragastric feeding.

Example 1

Effects of Yeast Compositions on Sexual Function of Castrated Male Wistar Rats

To test the ability of the EMF-treated AS2.502 cells to improve male sexual function, hormone levels, and sexual organ development, 50 healthy adult male Wistar rats (about 100–120 g body weight, 6–8 weeks old) were selected. Ten rats were randomly selected to be the normal control group, CK1 (uncastrated rats). Under anesthesia with pentobarbital (5%, at 45 mg/kg body weight), both testes (including the epididymis) of each of the remaining 40 rats were removed under sterile conditions. Immediately after castration, Penicillin G was injected at 20,000 U/kg body weight once daily for five consecutive days. The castrated rats were then randomly divided into four equal groups, designated as AY (for treatment with the activated yeast composition), NY (for treatment with the control yeast composition), CK2 (for treatment with testosterone propionate), and CK3 (for treatment with saline). Each rat was kept separately. The activated yeast composition was administered to the AY rats at 1.2 ml/kg body weight once daily for 30 days. The control yeast composition was administered to the NY rats and saline was administered to the CK3 rats at the same dosage. Testosterone propionate was injected intramuscularly to the CK2 rats in the buttocks at 2 mg/kg once daily for 30 days.

The uncastrated CK1 rats, each also kept separately, were administered 1.2 ml/kg of saline once daily for 30 days.

On the twenty-ninth day of the experiment, two female rats (100–120 g, 6–8 weeks old) were put into the same cage as each male rat and kept there for 30 minutes. The frequency of the male rat's sniffing and licking of the female rats, and the frequency of the male rat's mounting of the female rats were recorded in Table 2.

Each male rat was sacrificed on the thirty-first day. The seminal vesicle and prostate were retrieved and placed in Bouin's solution overnight. The fatty tissue around the seminal vesicle and the prostate was removed. The ductus deferens, part of the urethra, and the bladder were also removed from the peripheries of the seminal vesicle and the prostate. The remaining seminal vesicle and the prostate were weighed and then submerged in 70% ethanol overnight. The urethra was then completely stripped away from the prostate and seminal vesicle. The wet weight of the prostate and seminal vesicle was recorded in Table 2. The oval-shaped glandulae preputiales was also retrieved from the pubis area. The wet weight of the glandulae preputiales was also recorded in Table 2.

TABLE 2

Effects of Yeast Compositions on Male Sexual Activity, Glandulae Preputiales, Seminal Vesicle and Prostate of Castrated Wistar Rats

| Group (10 rats each) | Composition Used | Mounting Frequency Within a 30 min Period | Sniffing & Licking Frequency Within a 30 min Period | Glandulae Preputiales (mg) | Seminal Vesicle and Prostate (mg) |
|---|---|---|---|---|---|
| AY | activated yeast | 16.7 ± 2.3 | 38.7 ± 4.1 | 93.7 ± 18.6 | 303.8 ± 44.3 |
| NY | control yeast | 4.2 ± 1.4 | 8.6 ± 3.4 | 48.6 ± 11.4 | 51.6 ± 23.4 |
| CK1 | saline | 21.4 ± 1.5 | 46.6 ± 3.3 | 102.3 ± 22.4 | 393.6 ± 78.3 |
| CK2 | testosterone propionate | 12.3 ± 4.6 | 22.7 ± 4.6 | 89.5 ± 14.6 | 198.7 ± 42.6 |
| CK3 | saline | 3.5 ± 1.1 | 9.3 ± 2.7 | 43.5 ± 12.1 | 47.3 ± 26.7 |

The results in Table 2 show that (1) the activated yeast composition was capable of restoring sexual function/activity in castrated male rats, while the control yeast composition or saline was not; (2) the activated yeast composition stimulated the growth of the prostate, seminal vesicle and glandulae preputiales in castrated rats, while the control yeast composition or saline did not; and (3) the activated yeast composition was superior to testosterone propionate in stimulating the growth of the prostate, seminal vesicle and glandulae preputiales.

Example 2

Effects of Yeast Compositions on Erectile Function and Testosterone Levels of Castrated Wistar Rats To test the ability of the EMF-treated AS2.502 cells to improve male sexual function, hormone levels, and sexual organ development, 50 healthy adult male Wistar rats (about 150–180 g body weight, 8–10 weeks old) were selected. Ten rats were randomly selected to be the normal control group, CK1 (uncastrated rats). Under anesthesia with pentobarbital (5%, at 45 mg/kg body weight), both testes (including the epididymis) of each of the remaining 40 rats were removed under sterile conditions. Immediately after castration, Penicillin G was injected at 20,000 U/kg body weight once daily for five consecutive days. The castrated rats were then randomly divided into four equal groups, designated as AY (for treatment with the activated yeast composition), NY (for treatment with the control yeast composition), CK2 (for treatment with testosterone propionate), and CK3 (for treatment with saline). Each rat was kept separately. The activated yeast composition was administered to the AY rats at 1.2 ml/kg body weight once daily for 30 days. The control yeast composition was administered to the NY rats and saline was administered to the CK3 rats at the same dosage. Testosterone propionate was injected intramuscularly to the CK2 rats in the buttocks at 2 mg/kg once daily for 30 days. The uncastrated CK1 rats, each also kept separately, were administered 1.2 ml/kg of saline once daily for 30 days.

On the thirty-first day of the experiment, an electrical stimulator was used to measure the erectile function of the rats. One of the two electrodes of the electric stimulator was placed at the opening of urethra, and the other in contact with the skin of the penis shaft. The stimulator was switched on at 55 Hz and 4.5 mA. The time needed for the penis to achieve erection ("the erection lag") was recorded in Table 3.

Each rat was sacrificed after the erection test. Blood samples were collected from each rat, and the blood concentration of testosterone was determined by the standard radio-immunoassay (RIA) method. The results are shown in Table 3 below.

TABLE 3

Effects of Yeast Compositions on Erectile Function and Testosterone Levels of Castrated Wistar Rats

| Group (10 rats each) | Composition used | Erection Lag (second) | Testosterone Levels (ng/dl) |
|---|---|---|---|
| AY | activated yeast | 18.7 ± 10.2 | 138.72 ± 64.15 |
| NY | control yeast | 28.2 ± 14.5 | 58.66 ± 23.43 |
| CK1 | saline | 15.4 ± 9.6 | 156.54 ± 72.43 |
| CK2 | testosterone propionate | 19.3 ± 14.6 | 124.17 ± 67.65 |
| CK3 | saline | 27.5 ± 15.4 | 49.38 ± 22.76 |

The results in Table 3 show that the activated yeast compositions shortened erection lag and increased the secretion of testosterone, while the control yeast composition or saline did not.

While a number of embodiments of this invention have been set forth, it is apparent that the basic constructions may be altered to provide other embodiments which utilize the compositions and methods of this invention.

What is claimed is:

1. A method of preparing a yeast composition, comprising culturing a plurality of yeast cells of *Saccharomyces cerevisiae* Hansen AS2.502 in the presence of an alternating electric field having a frequency in the range of about 7900 to 13200 MHz and a field strength in the range of about 240 to 500 mV/cm for 60–168 hours.

2. The method of claim 1, wherein said frequency is in the range of about 7900–8000, 12700–12800, or 13050–13200 MHz.

3. The method of claim 1, wherein said field strength is in the range of about 260–280, 290–320, 300–320, 310–340, 330–360, 350–380, 360–400, or 420–460 mV/cm.

4. The method of claim 1, wherein said composition is in the form of a tablet, powder, or a health drink.

5. The method of claim 1, wherein said composition is in the form of a health drink.

* * * * *

UNITED STATES PATENT AND TRADEMARK OFFICE
CERTIFICATE OF CORRECTION

PATENT NO.         : 7,259,001 B2
APPLICATION NO. : 10/717158
DATED              : August 21, 2007
INVENTOR(S)        : Ling Y. Cheung It is certified that error appears in the above-identified patent and that said Letters Patent is hereby corrected as shown below:

Column 2, line 2: "AS2.3 11" should read -- AS2.311 --.

Column 11, line 39: "$KH2PO4$" should read -- $KH_2PO_4$ --.

Signed and Sealed this

Eleventh Day of December, 2007

JON W. DUDAS
*Director of the United States Patent and Trademark Office*